(12) United States Patent
Bogaerts

(10) Patent No.: US 12,708,573 B2
(45) Date of Patent: Aug. 18, 2026

(54) ADHESIVE TAPE ASSEMBLIES

(71) Applicant: Avery Dennison Corporation, Mentor, OH (US)

(72) Inventor: Bert Bogaerts, Boechout (BE)

(73) Assignee: Avery Dennison Corporation, Mentor, OH (US)

( * ) Notice: Subject to any disclaimer, the term of this patent is extended or adjusted under 35 U.S.C. 154(b) by 193 days.

(21) Appl. No.: 18/248,886

(22) PCT Filed: Oct. 15, 2021

(86) PCT No.: PCT/US2021/055190

§ 371 (c)(1),
(2) Date: Apr. 13, 2023

(87) PCT Pub. No.: WO2022/081979

PCT Pub. Date: Apr. 21, 2022

(65) Prior Publication Data

US 2023/0390126 A1 Dec. 7, 2023

Related U.S. Application Data

(60) Provisional application No. 63/188,304, filed on May 13, 2021, provisional application No. 63/092,626, filed on Oct. 16, 2020.

(51) Int. Cl.

*A61F 13/58* (2006.01)
*B32B 3/06* (2006.01)

(Continued)

(52) U.S. Cl.

CPC ................ *A61F 13/58* (2013.01); *B32B 3/06* (2013.01); *B32B 5/022* (2013.01); *B32B 27/12* (2013.01);

(Continued)

(58) Field of Classification Search

CPC ........... A61F 13/58; B32B 3/06; B32B 5/022; B32B 27/12; B32B 37/12; C09J 7/203;

(Continued)

(56) References Cited

U.S. PATENT DOCUMENTS 5,182,156 A 1/1993 Pape et al.
5,234,517 A 8/1993 Pape et al.

(Continued)

FOREIGN PATENT DOCUMENTS

BR 202013018562 U2 11/2015
CA 2496284 11/2008

(Continued)

OTHER PUBLICATIONS

International Preliminary Report on Patentability dated Apr. 13, 2023 issued in corresponding IA No. PCT/US2021/055190 filed Oct. 15, 2021.

(Continued)

*Primary Examiner* — Patricia L. Nordmeyer

(57) ABSTRACT

An improved fastener tape assembly is shown and described. The fastener tape assembly includes a carrier component including a non-woven layer, a polymer film layer, an adhesive layer, and a release. The fastener tape assembly described herein may also be included in a z-fold assembly.

29 Claims, 10 Drawing Sheets

(51) Int. Cl.

| | |
|---|---|
| ***B32B 5/02*** | (2006.01) |
| ***B32B 27/12*** | (2006.01) |
| ***B32B 37/12*** | (2006.01) |
| ***C09J 7/20*** | (2018.01) |
| ***C09J 7/29*** | (2018.01) |
| ***C09J 109/06*** | (2006.01) |

(52) U.S. Cl.
CPC ................. *C09J 7/203* (2018.01); *C09J 7/29* (2018.01); *C09J 109/06* (2013.01); *B32B 37/12* (2013.01); *C09J 2301/18* (2020.08); *C09J 2301/302* (2020.08)

(58) Field of Classification Search
CPC ........ C09J 7/29; C09J 109/06; C09J 2301/18; C09J 2301/302; C09J 153/02; C09J 2301/122; C09J 2400/263; C09J 2423/006; C09J 2433/00; C09J 2453/00; C09J 2483/00
See application file for complete search history.

(56) References Cited

U.S. PATENT DOCUMENTS

| | | | |
|---|---|---|---|
| 5,591,521 A | 1/1997 | Arakawa et al. | |
| 6,129,964 A | 10/2000 | Seth | |
| 6,264,644 B1 | 7/2001 | Igaue et al. | |
| 6,524,294 B1 | 2/2003 | Hilston et al. | |
| 6,656,171 B1 | 12/2003 | Matsuda et al. | |
| 7,132,031 B2 | 11/2006 | Ohiro et al. | |
| 7,435,245 B2 | 10/2008 | Wendelstorf et al. | |
| 7,892,219 B2 | 2/2011 | Ito et al. | |
| 8,034,040 B2 | 10/2011 | Sasaki et al. | |
| 10,085,897 B2 | 10/2018 | Landgrebe et al. | |
| 11,060,654 B2 * | 7/2021 | Shuey | B32B 27/065 |
| 2001/0023341 A1 | 9/2001 | Karami | |
| 2003/0004486 A1 | 1/2003 | Suzuki et al. | |
| 2003/0014030 A1 | 1/2003 | Andersson et al. | |
| 2003/0032359 A1 | 2/2003 | Kinnear et al. | |
| 2004/0138639 A1 | 7/2004 | Ito et al. | |
| 2004/0267227 A1 | 12/2004 | Ito et al. | |
| 2005/0079372 A1 | 4/2005 | Schmal et al. | |
| 2005/0277905 A1 | 12/2005 | Pedersen et al. | |
| 2007/0286976 A1 | 12/2007 | Selen et al. | |
| 2008/0103470 A1 | 5/2008 | Samuelsson et al. | |
| 2011/0301563 A1 | 12/2011 | Maruhata et al. | |
| 2014/0010984 A1 | 1/2014 | Bogaerts et al. | |
| 2019/0076308 A1 | 3/2019 | Ikishima et al. | |
| 2019/0117480 A1 | 4/2019 | Bogaerts et al. | |
| 2019/0350778 A1 | 11/2019 | Qi et al. | |
| 2020/0030164 A1 | 1/2020 | Matsuda et al. | |
| 2021/0000664 A1 | 1/2021 | Bogaerts | |

FOREIGN PATENT DOCUMENTS

| | | | |
|---|---|---|---|
| CN | 1153466 | 7/1997 | |
| CN | 103648463 | 3/2014 | |
| CN | 106659619 | 5/2017 | |
| CN | 110352049 | 10/2019 | |
| EP | 0191355 | 4/1989 | |
| EP | 1002846 | 4/2004 | |
| EP | 1762207 | 3/2007 | |
| EP | 3007664 | 4/2018 | |
| EP | 3797747 | 3/2021 | |
| JP | 5-117607 | 5/1993 | |
| JP | 7-157728 | 6/1995 | |
| JP | 2000-503228 | 3/2000 | |
| JP | 2006-045417 | 2/2006 | |
| JP | 2012-143432 | 8/2012 | |
| JP | 2012-152323 | 8/2012 | |
| JP | 2012-165857 | 9/2012 | |
| JP | 2013-118923 | 6/2013 | |
| JP | 5696497 | 4/2015 | |
| JP | 5967231 | 8/2016 | |
| JP | 2018-121931 | 8/2018 | |
| JP | 2018-145357 | 9/2018 | |
| JP | 2019-218420 | 12/2019 | |
| WO | WO-9306183 A1 * | 4/1993 | B32B 27/08 |
| WO | 96/02218 | 2/1996 | |
| WO | 2007/032965 | 3/2007 | |
| WO | 2008/156931 | 12/2008 | |
| WO | 2012/129428 | 9/2012 | |
| WO | 2013/086320 | 6/2013 | |
| WO | 2015/066210 | 5/2015 | |
| WO | 2016/007703 | 1/2016 | |
| WO | 2017/069050 | 4/2017 | |
| WO | 2018/133026 | 7/2018 | |
| WO | 2018/142255 | 8/2018 | |
| WO | 2019/173297 | 9/2019 | |
| WO | 2021/064555 | 4/2021 | |

OTHER PUBLICATIONS

International Search Report and Written Opinion dated Feb. 24, 2022 issued in corresponding IA No. PCT/US2021/055190 filed Oct. 15, 2021.

* cited by examiner 200
201
202
203
214
211
214
210
224
206
207
221
226
219
225
220
227
223
222
205
217
216
204
218
217
213
208
212
209

ADHESIVE TAPE ASSEMBLIES

CROSS REFERENCE TO RELATED APPLICATIONS

The present application is a 371 of international Application No. PCT/US2021/055190, which was published in English on Apr. 21, 2022, and claims the benefit of U.S. Provisional Application Nos. 63/092,626 filed Oct. 16, 2020 and 63/188,304 filed May 13, 2021, the disclosures of which are incorporated by reference herein in their entireties.

FIELD

The present invention relates generally to fastening tabs that may be found in connection with disposable absorbent articles such as diapers, as well as other applications, specifically adhesive tape assemblies. The invention thus provides enhanced or improved capabilities for adhesive tape assemblies.

BACKGROUND

Fastening tabs may be found in connection with disposable absorbent articles such as diapers, as well as other applications. Disposable absorbent articles, such as baby diapers and/or incontinence diapers for adults, are generally known in the art. A disposable article (for example, a diaper chassis), in many instances, is constructed of a liquid absorbent core (promoting separation of fluid from the user) enclosed between a liquid permeable topsheet (located adjacent to a wearer when the disposable article is worn) and a liquid impermeable backsheet (forming an outer surface of the disposable article when worn, which may be a nonwoven fabric laminated with a water impermeable layer such as a polyethylene film). The disposable article generally includes a rear portion intended to cover a wear's behind, a front portion intended to cover a wear's front and a crotch portion there-between.

Disposable articles are available in reusable form which must be washed between uses, or may be one-time use disposable forms. Disposable forms include one or more adhesive tape assemblies which are typically used to maintain a used diaper in a "rolled-up" form after use to facilitate handling and disposal. This disposal tape will need to bond to the outside of a diaper. However, the outer surface of diapers has been designed to be increasingly softer, which then requires soft, but aggressive adhesives that bond well to the nonwoven portions of the diaper. While the bonding adhesive of the disposal tape can create an acceptable bond to a nonwoven diaper backsheet, it can cause problems, such as blocking, in rolls of the adhesive tape assemblies.

Conventional disposal tapes are typically stored in rolls. Such conventions disposal tapes include a nonwoven layer having a release layer on one surface of the nonwoven, and a polymer layer on the opposite surface of the nonwoven, as well as an adhesive layer disposed on the surface of the polymer layer facing away from the nonwoven. This disposal tape configuration is prone to blocking, or damage to the tape upon removal of one layer of disposal tape from an adjacent layer of the tape. Although the release layer is designed to protect the underlying structure, due to the absorbent nature of the nonwoven, the release layer does not provide full coverage of the underlying nonwoven layer. As a result, a portion of the adhesive layer tends to penetrate into the adjacent nonwoven material. Upon removal of one layer of tape from an adjacent tape layer, for example when unwinding a roll of tape or removing a sheet of tape, the release force increases, and some nonwoven fibers are undesirably pulled out from the nonwoven material as the adhesive layer is released from the nonwoven. This causes damage to the tape, and prevents the tape from unwinding cleanly from a roll. In some circumstances, the tape may even break, or it may not be possible to unwind the tape fully without destroying the tape.

Securing a fastener to a disposable article is typically performed so as to provide a strong and durable affixment. Several techniques have been used to provide such an affixment, including mechanical bonding procedures and the use of high strength adhesives. However, there can be difficulties in developing a fastening system that can achieve a limited degree of elongation and/or stretch. Such limitations on the degree of elongation and/or stretch are desirable in particular for diapers designed for children, as a significantly elongatable fastener can pose a strangulation hazard for young children. Some jurisdictions have instituted regulations that limit the allowable total elongation of fastener systems, for example some international toy regulations restrict the allowable total elongation to less than 200 mm. A means to reduce the amount of elongation of fastener tape assemblies, yet provide a typical strength of fastener tape assemblies, would be desirable. Further, more flexibility due to a thinner film than that of current systems would also be desirable. Additionally, less plastic deformation than is provided by the current cast polypropylene (PP) constructions and the accompanying improved aesthetics when the tape is applied to the diaper, would be desirable as well. Still further, a tape that does not exhibit blocking is desired. Accordingly, a need remains for fastener tape assemblies with at least one of these properties.

SUMMARY

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Improved fastener tape assemblies are shown and described. The fastener tape assembly comprises: (1) a carrier component including: (a) a non-woven layer having a first side and a second side; and (b) a polymer film layer having a first side and a second side; wherein the second side of the polymer film layer is at least partially disposed on the first side of the non-woven layer; (2) an adhesive layer at least partially disposed on the second side of the non-woven layer; and (3) a release layer at least partially disposed on the first side of the polymer film layer. In many embodiments, the carrier component is extrusion laminated, adhesive bonded, or combinations thereof. In many embodiments, the non-woven layer includes a spunbond non-woven, carded non-woven, spunlace non-woven, meltblown non-woven, or combinations thereof. Other types of non-wovens are contemplated as well. In several embodiments, the polymer film includes a polyolefin. In many embodiments, the adhesive layer includes acrylic adhesive, rubber adhesive, silicone adhesive, or combinations thereof. In many embodiments, the rubber adhesive includes Poly(styrene-butadiene-styrene) (SBS), poly(styrene-isoprene-styrene) (SIS), styrene-butadiene (SB), or combinations thereof. In many embodiments, the adhesive layer is pressure sensitive. In many embodiments, the adhesive layer is patterned. In many embodiments, the adhesive layer is continuous. In many embodiments the release layer includes a silicone, a fluoropolymer, or combinations thereof. In many embodiments, the release layer is at least partially bonded to the first side of the polymer film layer using heat. In many embodiments, the silicone release layer is at least partially bonded to the first side of the polymer film layer using UV or IR curing.

Also described is a z-fold fastener tape assembly including: (1) a fastening component defining a first face for affixment to a disposable article or substrate and an oppositely directed second face; (2) a bonding component defining a first face for affixment to a disposable article or substrate and an oppositely directed second face; and (3) an extension component generally disposed between the fastening component and the bonding component and at least partially attached to the fastening component and to the bonding component; wherein at least one of the fastening component, the bonding component, and the extension component includes the fastener tape assembly described herein.

Also described is a z-fold fastener tape assembly including: (1) a fastening component defining a first face for affixment to a disposable article or substrate and an oppositely directed second face; (2) a bonding component defining a first face for affixment to a disposable article or substrate and an oppositely directed second face; and (3) an extension component generally disposed between the fastening component and the bonding component and at least partially attached to the fastening component and to the bonding component; wherein the fastening component includes: (i) a carrier component including: (a) a non-woven layer having a first side and a second side; and (b) a polymer film layer having a first side and a second side; wherein the second side of the polymer film layer is at least partially disposed on the first side of the non-woven layer; (ii) an adhesive layer at least partially disposed on the second side of the non-woven layer; and (iii) a release layer at least partially disposed on the first side of the polymer film layer.

Further described is a z-fold fastener tape assembly including: (1) a fastening component defining a first face for affixment to a disposable article or substrate and an oppositely directed second face; (2) a bonding component defining a first face for affixment to a disposable article or substrate and an oppositely directed second face; and (3) an extension component generally disposed between the fastening component and the bonding component and at least partially attached to the fastening component and to the bonding component; wherein the bonding component includes: (i) a carrier component including: (a) a non-woven layer having a first side and a second side; and (b) a polymer film layer having a first side and a second side; wherein the second side of the polymer film layer is at least partially disposed on the first side of the non-woven layer; (ii) an adhesive layer at least partially disposed on the second side of the non-woven layer; and (iii) a release layer at least partially disposed on the first side of the polymer film layer.

Additionally, a z-fold fastener tape assembly is described including: (1) a fastening component defining a first face for affixment to a disposable article or substrate and an oppositely directed second face; (2) a bonding component defining a first face for affixment to a disposable article or substrate and an oppositely directed second face; and (3) an extension component generally disposed between the fastening component and the bonding component and at least partially attached to the fastening component and to the bonding component; wherein the extension component includes: (i) a carrier component including: (a) a non-woven layer having a first side and a second side; and (b) a polymer film layer having a first side and a second side; wherein the second side of the polymer film layer is at least partially disposed on the first side of the non-woven layer; (ii) an adhesive layer at least partially disposed on the second side of the non-woven layer; and (iii) a release layer at least partially disposed on the first side of the polymer film layer.

Further described is a z-fold fastener tape assembly including: a fastening component defining a first face for affixment to a disposable article or substrate and an oppositely directed second face; a bonding component defining a first face for affixment to a disposable article or substrate and an oppositely directed second face; and an extension component generally disposed between the fastening component and the bonding component and at least partially attached to the fastening component and to the bonding component; wherein the extension component includes a first face and a second face; wherein the extension component is substantially non-extendable; and wherein at least one of the fastening component and the bonding component includes the fastener tape assembly described herein.

Also described is a method of making the z-fold fastener tape assembly described in the embodiments herein. Further described is an article including the z-fold fastener tape assembly of the embodiments herein. In many embodiments, the article is a diaper.

Other features and advantages of the present invention will become apparent to those skilled in the art from the following detailed description. It is to be understood, however, that the detailed description of the various embodiments and specific examples, while indicating preferred and other embodiments of the present invention, are given by way of illustration and not limitation. Many changes and modifications within the scope of the present invention may be made without departing from the spirit thereof, and the invention includes all such modifications.

BRIEF DESCRIPTION OF THE FIGURES

Advantages of embodiments of the present invention will be apparent from the following detailed description of the exemplary embodiments thereof, which description should be considered in conjunction with the accompanying drawings in which like numerals indicate like elements, in which.

DETAILED DESCRIPTION

Figure 1A:
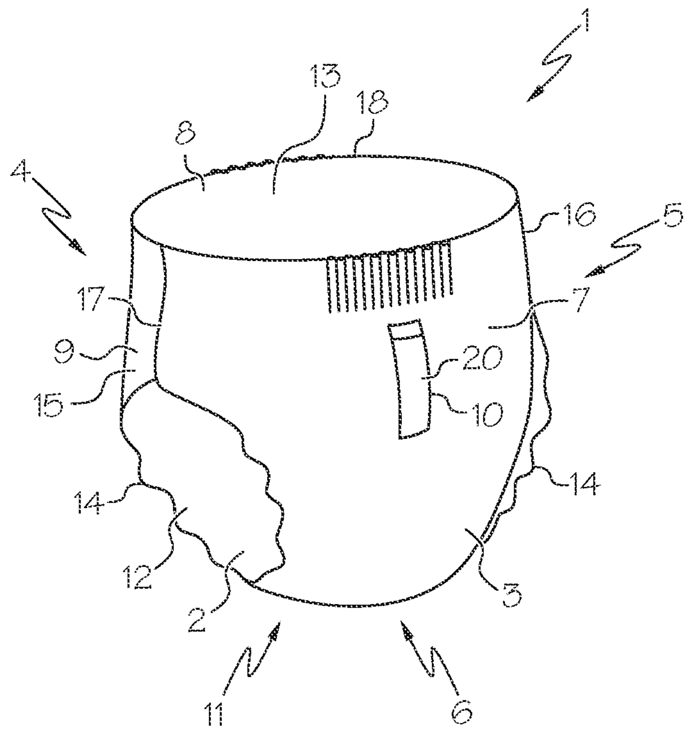
FIG. 1A is a schematic illustration showing a disposable article having attached thereto a fastening tab including the fastener tape assembly, according to aspects described herein.

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description, discussion of several terms used herein follows.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage or mode of operation.

The fastener tape assembly includes a carrier component. The carrier component includes a nonwoven layer, a polymer film layer, and an adhesive layer. The non-woven layer has a first side and an oppositely facing second side. The polymer film layer has a first side and an oppositely facing second side. In some embodiments, the second side of the polymer film layer is at least partially disposed on the first side of the non-woven layer. In some embodiments, the polymer film layer is fully or substantially fully disposed on the first side of the non-woven layer. In some embodiments, the adhesive layer is at least partially disposed on the second side of the non-woven layer. In some embodiments, the adhesive layer is fully or substantially fully disposed on the second side of the non-woven layer. In some embodiments, the release layer is at least partially disposed on the first side of the polymer film layer. In some embodiments, the release layer is fully or substantially fully disposed on the first side of the polymer film layer As previously noted, conventional tapes suffer from the disadvantage of blocking, due to an adhesive from one tape layer migrating into a nonwoven material on an adjacent tape layer. By "blocking" is meant herein the inability or impairment of the ability of one layer of a tape to be removed from another layer of the tape without defects, due to an increase in bond strength between the layers. In the absence of blocking, one layer of a tape can be removed from an adjacent tape layer easily, without requiring the application of a high amount of force. Blocking occurs when the bond between layers increases, requiring a higher amount of force to separate the layers. If the bond between layers is high enough, the unwinding process of a tape roll can stall. In some circumstances, the available tension can be concentrated in one or more locations on the tape, or at the tape edge, likely causing damage or breakage of the tape at or near those locations. It was unexpectedly discovered that blocking can be overcome by orienting the nonwoven layer between the polymer film and the adhesive layer, and placing the release layer on the side of the polymer layer that is opposite the side where the nonwoven resides. As a result, the adhesive layer of a first layer of the fastener tape assembly is separated from the nonwoven layer of a second, adjacent layer of the fastener tape assembly, by both the release layer and the polymer film. In this configuration, the adhesive cannot penetrate into the nonwoven layer of the second fastener tape assembly. Consequently, the nonwoven layer of the underlying second layer of the fastener tape assembly remains intact upon the removal of the adjacent first layer of the fastener tape assembly, as the nonwoven fibers of the underlying second layer are not pulled out by the adhesive of the first layer. Since blocking is reduced or does not occur, each layer of the fastener tape assembly can be cleanly or substantially cleanly removed from adjacent tape assembly layers.

The non-woven layer can be made of any suitable material. In many embodiments, the non-woven layer includes a spunbond non-woven, carded non-woven, spunlace non-woven, meltblown non-woven, or combinations thereof. The non-woven layer may also include other non-wovens not described herein. In many embodiments, the nonwoven has a thickness of a range of from 10 to 70 gsm (grams per square meter). In some embodiments, the nonwoven has a thickness of a range of from 20 to 60 gsm. In some embodiments, the nonwoven has a thickness of a range of from 30 to 50 gsm.

The polymer film can be made of any suitable material. In several embodiments, the polymer film includes a polyolefin, such as for example polypropylene, biaxially oriented polypropylene, polyethylene, or combinations thereof. In several embodiments, the polymer film includes polypropylene, biaxially oriented polypropylene, polyethylene, or combinations thereof. In many embodiments, the adhesive layer includes acrylic adhesive, rubber adhesive, silicone adhesive, or combinations thereof. In many embodiments, the polymer film includes polypropylene, biaxially oriented polypropylene, polyethylene, or combinations thereof. In many embodiments, the polymer film has a thickness of a range of from 5 to 50 gsm. In some embodiments, the polymer film has a thickness of a range of from 10 to 40 gsm. In other embodiments, the polymer film has a thickness of a range of from 15 to 35 gsm.

In many embodiments, the adhesive layer includes an acrylic adhesive, rubber adhesive, silicone adhesive, or combinations thereof. In some embodiments, the rubber adhesive includes poly(styrene-butadiene-styrene) (SBS), poly(styrene-isoprene-styrene) (SIS), styrene-butadiene (SB), or combinations thereof. In many embodiments, the adhesive layer is a pressure sensitive. In some embodiments, the adhesive layer is patterned. By "patterned" is meant herein that the adhesive is deposited in a configuration that is discontinuous, or forms a pattern. The pattern can be uniform, non-uniform, symmetrical or non-symmetrical. In some embodiments, the adhesive layer is continuous or substantially continuous.

The release layer can be made from any suitable material. In some embodiments, the release layer includes a silicone, a fluoropolymer, or a combination thereof. In some embodiments, the release layer includes silicone. Although a silicone release layer may be used, other release layers are contemplated. In some embodiments, the release layer is at least partially bonded to the first side of the polymer film layer using heat. In some embodiments, the release layer is fully or substantially fully bonded to the first side of the polymer film layer using heat. In some embodiments, the release layer is at least partially bonded to the first side of the polymer film layer using ultraviolet (UV) or infrared (IR) curing. In some embodiments, the release layer is fully or substantially fully bonded to the first side of the polymer film layer using UV or IR curing.

The force required to remove one layer of a tape from another is impacted by at least one of the type of adhesive and the amount of silicone in the tape. It was unexpectedly discovered that the amount of silicone needed for the present fastener tape assembly is significantly lower than that required for conventional tapes. In some embodiments, the fastener tape assembly has a release coat weight that is from 3 to 6 times less than the silicone coat weight of conventional nonwoven based tapes. In some embodiments, the release coat weight is less than 6 g/m2. In some embodiments, the release coat weight is less than 5 g/m2, less than 4 g/m2, less than 3 g/m2 or less than 2 g/m2.

In many embodiments, the carrier component can be manufactured using any suitable method. In some embodiments, the carrier component is extrusion laminated, adhesive bonded, or combinations thereof.

The fastener tape assembly can be in any suitable form. In some embodiments, the fastener tape assembly is in a roll form. In some embodiments, the fastener tape assembly is in a sheet form.

The fastener tape assembly can be used in any closure or disposal tape construction, for diapers or other articles. In some embodiments, the fastener tape assembly is included in at least a portion of a no-fold fastener tape or two-fold fastener tape assembly. In some embodiments, the no-fold fastener tape or two-fold fastener tape assembly can further include at least one mechanical closure mechanism, such as for example hooks.

In some embodiments, the fastener tape assembly of the disclosure is included in at least a portion of a z-fold fastener tape assembly. The z-fold fastener tape assembly includes a fastening component, a bonding component and an extension component disposed between the fastening component and the bonding component. At least one of the fastening component, the bonding component, and the extension component includes the fastener tape assembly described herein. In some embodiments, each of the fastening component, the bonding component, and the extension component includes the fastener tape assembly. In some embodiments, the fastening component includes the fastener tape assembly described herein.

In some embodiments, at least a portion of the fastening component of the z-fold fastening tape assembly is configured for attachment to a disposable article or a substrate. In some embodiments, the fastening component defines a first face for affixment to a disposable article or substrate and an oppositely directed second face. In some embodiments, at least a portion of the first face of the fastening component is configured for affixement to a disposal article or substrate. In some embodiments, all or substantially all of the first face of the fastening component is configured for affixement to a disposal article or substrate.

In some embodiments, at least a portion of the bonding component of the fastening tape assembly is configured for attachment to a disposable article or a substrate. In some embodiments, the bonding component defines a first face for affixment to a disposable article or substrate and an oppositely directed second face. In some embodiments, at least a portion of the first face of the bonding component is configured for affixement to a disposable article or substrate. In some embodiments, all or substantially all of the first face of the bonding component is configured for affixement to a disposable article or substrate.

The extension component is generally disposed between the fastening component and the bonding component. By "generally disposed between" is meant herein, at least a part of the extension component is situated between the fastening component and bonding component. In some embodiments, at least a portion of the extension component is at least partially attached to the fastening component. In some embodiments, at least a portion of the extension component is at least partially attached to the bonding component. In some embodiments, the extension component is directly attached to at least one of the fastening component and bonding component. For example, at least a portion of the extension component can be adhered to at least a portion of at least one of the fastening component and bonding component. In some embodiments, the extension component is indirectly attached to at least one of the fastening component and bonding component. For example, at least a portion of the extension component can be adhered to a different structure that is in turn adhered to the fastening component or the bonding component, forming, for example, a U-bond between the extension component and the fastening component or the bonding component.

In some embodiments, the fastening component of the z-fold fastener tape assembly includes a carrier component as described hereinabove. The carrier component includes a non-woven layer having a first side and a second side, a polymer film layer having a first side and a second side, an adhesive layer and a release layer. At least a portion of the second side of the polymer film layer is at least partially disposed on the first side of the non-woven layer. At least a portion of the adhesive layer is at least partially disposed on the second side of the non-woven layer. At least a portion of the release layer is at least partially disposed on the first side of the polymer film layer. In some embodiments, the adhesive layer of the fastening component is provided in an adhesive region on the first face of the fastening component. The fastening component is at least partially bonded to the extension component at the adhesive region. In some embodiments, the first face of the fastening component is at least partially covered by the adhesive layer to thereby bond the fastening component with the extension component. In some embodiments, the adhesive layer on the first face of the fastening component is patterned. In some embodiments, the adhesive layer on the first face of the fastening component is continuous. In some embodiments, a distal end of the fastening component is folded, thereby forming a folded edge. The fastening component is attached to the extension component at that folded edge. In some embodiments, a filmic strip is attached to a distal end of the fastening component, forming a U bond that connects the fastening component to the extension component. The filmic strip can be made of any suitable material having a high tear resistance, such as for example a cast polypropylene or PET filmic layer. In some embodiments, the adhesive layer is a pressure sensitive adhesive. In some embodiments, the fastening component further includes at least one mechanical closure mechanism, such as for example hooks. The at least one mechanical closure mechanism can be used to attach the fastener tape assembly to a diaper article or substrate. The at least one mechanical closure mechanism can be used in conjunction with an adhesive.

In some embodiments, the bonding component of the z-fold fastener tape assembly includes a carrier component as described hereinabove. The carrier component includes a non-woven layer having a first side and a second side, a polymer film layer having a first side and a second side, an adhesive layer and a release layer. At least a portion of the second side of the polymer film layer is at least partially disposed on the first side of the non-woven layer. At least a portion of the adhesive layer is at least partially disposed on the second side of the non-woven layer. At least a portion of the release layer is at least partially disposed on the first side of the polymer film layer. In some embodiments, the adhesive layer of the bonding component is provided in an adhesive region on the first face of the bonding component. The bonding component can be at least partially bonded to an article or substrate at the adhesive region. In some embodiments, the adhesive layer on the first face of the bonding component is patterned. In some embodiments, the adhesive layer on the first face of the bonding component is continuous. In some embodiments, the adhesive layer is a pressure sensitive adhesive. In some embodiments, a distal end of the bonding component is folded, thereby forming an edge, and the bonding component is attached to the extension component at that edge, forming a y-bond. In some embodiments, the first face of the bonding component is at least partially covered by the adhesive layer to thereby bond the bonding component with the extension component. In some embodiments, a filmic strip is attached to a distal end of the bonding component, forming a U bond that connects the bonding component to the extension component. The filmic strip can be made of any suitable material, such as for example a biaxially-oriented polypropylene (BOPP) filmic layer. In some embodiments, there is at least one perforation in the bonding component. In some embodiments, there is a plurality of perforations in the bonding component. In some embodiments, the at least one perforation is located on a y-bond joining the bonding component with the extension component. In some embodiments, the bonding component is attached to the extension component by two y-bonds, that are distanced one from the other, and one of the y-bonds includes at least one perforation. The perforations enable the bonding component to remain intact before use of the fastener tape assembly, and to be broken at the location of the perforations upon deployment of the fastener tape assembly. For example, perforations on the y-bond can reduce the risk of the bonding component and extension component swinging away from one another before deployment of the fastener tape assembly.

In some embodiments, the extension component of the z-fold fastener tape assembly includes a carrier component as described hereinabove. The carrier component includes a non-woven layer having a first side and a second side, and a polymer film layer having a first side and a second side, and adhesive layer and a release layer. At least a portion of the second side of the polymer film layer is at least partially disposed on the first side of the non-woven layer. At least a portion of the adhesive layer is at least partially disposed on the second side of the non-woven layer. At least a portion of the release layer is at least partially disposed on the first side of the polymer film layer. In some embodiments, the adhesive layer of the extension component is provided in an adhesive region on the first face of the extension component. The extension component is at least partially bonded to the bonding component at the adhesive region. In some embodiments, the first face of the extension component is at least partially covered by the adhesive layer to thereby bond the extension component with the bonding component. In some embodiments, the adhesive layer on the first face of the extension component is patterned. In some embodiments, the adhesive layer on the first face of the extension component is continuous. In some embodiments, the second face of the extension component is at least partially covered by the adhesive layer to thereby bond the extension component with the fastening component. In some embodiments, the adhesive layer on the second face of the extension component is patterned. In some embodiments, the adhesive layer on the second face of the extension component is continuous. In some embodiments, a distal end of the extension component is folded, thereby forming an edge, and the fastening component is attached to the extension component at that edge, forming a y-bond. In some embodiments the extension component is provided in an adhesive region on the first face of the extension component to thereby at least partially bond the bonding component with the extension component. In some embodiments, a first distal end of the extension component is folded, thereby forming an edge, and the fastening component is attached to the extension component at that edge, forming a first y-bond; and a second distal end of the extension component is folded, thereby forming an edge, and the fastening component is attached to the extension component at that edge, forming a second y-bond. In some embodiments the extension component is provided in an adhesive region on the first face of the extension component to thereby at least partially bond the extension component with the fastening component and the bonding component. In some embodiments, a filmic strip is attached to a distal end of the extension component, forming a U bond that connects the extension component to the fastening component or bonding component. The filmic strip can be made of any suitable material, such as for example a biaxially-oriented polypropylene (BOPP) filmic layer. In some embodiments, the adhesive layer is a pressure sensitive adhesive.

In some embodiments, the z-fold fastener tape assembly includes: (1) a fastening component defining a first face for affixment to a disposable article or substrate and an oppositely directed second face; (2) a bonding component defining a first face for affixment to a disposable article or substrate and an oppositely directed second face; and (3) an extension component generally disposed between the fastening component and the bonding component and at least partially attached to the fastening component and to the bonding component; wherein at least one of the fastening component, the bonding component, and the extension component includes the fastener tape assembly described herein.

In some embodiments, the z-fold fastener tape assembly includes: (1) a fastening component defining a first face for affixment to a disposable article or substrate and an oppositely directed second face; (2) a bonding component defining a first face for affixment to a disposable article or substrate and an oppositely directed second face; and (3) an extension component generally disposed between the fastening component and the bonding component and at least partially attached to the fastening component and to the bonding component; wherein the fastening component includes: (i) a carrier component comprising: (a) a nonwoven layer having a first side and a second side; and (b) a polymer film layer having a first side and a second side; wherein the second side of the polymer film layer is at least partially disposed on the first side of the non-woven layer; (ii) an adhesive layer at least partially disposed on the second side of the non-woven layer; and (iii) a release layer at least partially disposed on the first side of the polymer film layer.

In many embodiments, the carrier component of the z-fold fastener tape assembly can be manufactured using several different methods. In some embodiments, the carrier component is extrusion laminated, adhesive bonded, or combinations thereof.

The non-woven layer of the z-fold fastener tape assembly can be made of any suitable material. In many embodiments, the non-woven layer includes a spunbond non-woven, carded non-woven, spunlace non-woven, meltblown non-woven, or combinations thereof. The non-woven layer can also include other non-wovens not described herein. In many embodiments, the nonwoven has a thickness of a range of from 10 to 70 gsm. In some embodiments, the nonwoven has a thickness of a range of from 20 to 60 gsm. In some embodiments, the nonwoven has a thickness of a range of from 30 to 50 gsm.

The polymer film of the z-fold fastener tape assembly can be made of any suitable material. In many embodiments, the polymer film includes polypropylene, biaxially oriented polypropylene, polyethylene, or combinations thereof. In many embodiments, the polymer film has a thickness of a range of from 5 to 50 gsm. In some embodiments, the polymer film has a thickness of a range of from 10 to 40 gsm. In many embodiments, the polymer film has a thickness of a range of from 15 to 35 gsm.

The adhesive layer of the carrier component in the z-fold fastener tape assembly can be made of any suitable material. In many embodiments, the adhesive layer includes acrylic adhesive, rubber adhesive, silicone adhesive, or combinations thereof. In some embodiments, the rubber adhesive comprises Poly(styrene-butadiene-styrene) (SBS), poly(styrene-isoprene-styrene) (SIS), or combinations thereof. In many embodiments, the adhesive layer is pressure sensitive. In some embodiments, the adhesive layer is patterned, as described herein-above. In some embodiments, the adhesive layer is continuous.

The release layer of the carrier component in the z-fold fastener tape assembly can be made of any suitable material. In some embodiments, the release layer includes, a silicone. The release layer can be bonded to the polymer film by any suitable method. In some embodiments, the release layer is at least partially bonded to the first side of the polymer film layer using heat. In some embodiments, the release layer is at least partially bonded to the first side of the polymer film layer using UV or IR curing.

In some embodiments, the z-fold fastener tape assembly includes a finger lift that is at least partially affixed to the fastening component. In some embodiments, at least a portion of at least one surface of the fingerlift is adhesive-free. In some embodiments, at least a portion of both surfaces of the fingerlift are adhesive-free. In some embodiments, the fingerlift is substantially adhesive-free. The fingerlift provides an extended tab that can be grasped by a user, enabling the user to easily open the z-fold fastener tape assembly.

In many embodiments, the fastener tape assembly of the z-fold fastener tape assembly is in a roll form. In many embodiments, the fastener tape assembly of the z-fold fastener tape assembly is in a sheet form.

In some embodiments, the z-fold fastener tape assembly includes: (1) a fastening component defining a first face for affixment to a disposable article or substrate and an oppositely directed second face; (2) a bonding component defining a first face for affixment to a disposable article or substrate and an oppositely directed second face; and (3) an extension component generally disposed between the fastening component and the bonding component and at least partially attached to the fastening component and to the bonding component; wherein the bonding component comprises: (i) a carrier component comprising: (a) a non-woven layer having a first side and a second side; and (b) a polymer film layer having a first side and a second side; wherein the second side of the polymer film layer is at least partially disposed on the first side of the non-woven layer; (ii) an adhesive layer at least partially disposed on the second side of the non-woven layer; and (iii) a release layer at least partially disposed on the first side of the polymer film layer.

In some embodiments, the z-fold fastener tape assembly includes: (1) a fastening component defining a first face for affixment to a disposable article or substrate and an oppositely directed second face; (2) a bonding component defining a first face for affixment to a disposable article or substrate and an oppositely directed second face; and (3) an extension component generally disposed between the fastening component and the bonding component and at least partially attached to the fastening component and to the bonding component; wherein the extension component comprises: (i) a carrier component comprising: (a) a non-woven layer having a first side and a second side; and (b) a polymer film layer having a first side and a second side; wherein the second side of the polymer film layer is at least partially disposed on the first side of the non-woven layer; (ii) an adhesive layer at least partially disposed on the second side of the non-woven layer; and (iii) a release layer at least partially disposed on the first side of the polymer film layer.

In many embodiments, at least one of the fastening component, extension component or bonding component is non-extendable or substantially non-extendable. By "non-extendable" is meant herein that after the yield point (end of elastic stretching), there is no plastic deformation or material flow, thus after the yield point, the film will break. When attached to an article or substrate, the bonding component can be partially, fully or substantially fully attached to the article or substrate. When the bonding component is fully or substantially fully attached to an article or substrate, the bonding component has little to no influence on the fastening tape assembly elongation. In many embodiments, the extension component is non-extendable or substantially non-extendable. In many embodiments, the fastening component and the extension component are non-extendable or substantially non-extendable. When both the fastening component and extension component are non-extendable, the total elongation of the fastening tape assembly upon exertion of an elongating force is even smaller than the total elongation when only the extension component is non-extendable or substantially non-extendable. By "total elongation" is meant herein the sum of an original length and any additional length resulting from the application of an elongating force.

In some embodiments, the z-fold fastener tape assembly extension component is non-extendable or substantially non-extendable, and the fastening component includes the fastener tape assembly described herein. In some embodiments, the z-fold fastener tape assembly includes: a fastening component defining a first face for affixment to a disposable article or substrate and an oppositely directed second face; a bonding component defining a first face for affixment to a disposable article or substrate and an oppositely directed second face; and an extension component generally disposed between the fastening component and the bonding component and at least partially attached to the fastening component and to the bonding component; wherein the extension component is substantially non-extendable; and wherein at least one of the fastening component and the bonding component includes the fastener tape assembly described herein.

In many embodiments, the z-fold fastener tape assembly is able to be stretched or elongated no more than 1%, no more than 2.5%, no more than 5%, no more than 10%, no more than 20%, no more than 25%, or no more than 35%, beyond its original length. In many embodiments, the z-fold tape assembly is able to be stretched or elongated to a total elongation of no more than 200 mm. In some embodiments, the z-fold tape assembly has a total elongation of less than 200 mm after elongation at an elongation speed of 1500 mm/min until rupture or break of the z-fold tape assembly.

The non-extendable or substantially non-extendable extension component can be made of any suitable material, such as for example an oriented film. In some embodiments, the extension component includes a polyester. In some embodiments, the extension component includes polyethylene terephthalate (PET), oriented polypropylene (OPP), BOPP, a blown film or any combination thereof. In some embodiments, the extension component includes polyethylene terephthalate (PET), oriented polypropylene (OPP), BOPP, or any combination thereof. In many embodiments, the non-extendable or substantially non-extendable extension component is a reinforced film or a laminate. In many embodiments, the non-extendable or substantially non-extendable extension component has a tear resistance, as measured by the Elmendorth tear strength test, of at least 200 millinewtons. In many embodiments, the non-extendable or substantially non-extendable extension component has a tear resistance, as measured by the Elmendorth tear strength test, of at least 400 millinewtons, or at least 500 millinewtons. In many embodiments, at least one of the extension component and fastener component is inelastic or substantially inelastic. In many embodiments the extension component is inelastic or substantially inelastic. The non-extendable nature of at least one of the fastening component and extension component restricts the deployment length of the z-fold fastener tape assembly. This is advantageous, as it provides for improved safety associated with the use of the tape assembly, or of any article on which the tape assembly is placed, particularly when the tape is used for articles designed for children. In many embodiments, the fastener tape assembly complies with International Organization for Standardization's ISO 8124 toy safety standards.

In many embodiments the non-extendable or substantially non-extendable extension component is at least partially covered by an adhesive on a first face of the extension component, and at least partially covered by a release layer on a second face of the extension component. In many embodiments the non-extendable or substantially non-extendable fastening component is at least partially covered by an adhesive on a first face of the fastening component, and at least partially covered by a release layer on a second face of the fastening component. In many embodiments, the adhesive layer includes acrylic adhesive, rubber adhesive, silicone adhesive, or combinations thereof. In some embodiments, the rubber adhesive includes poly(styrene-butadiene-styrene) (SBS), poly(styrene-isoprene-styrene) (SIS), or combinations thereof. In many embodiments, the adhesive layer is pressure sensitive. In some embodiments, the adhesive layer is patterned. In some embodiments, the adhesive layer is continuous. In some embodiments, the adhesive layer is a pressure sensitive adhesive.

The z-fold fastener tape assembly described in the disclosure can be made by any suitable method. The z-fold fastener tape assembly can be included on an article. In many embodiments, the article is a diaper.

FIG. 1A illustrates an embodiment of a disposable article 1 in accordance with the present subject matter. Referring to FIG. 1A disposable article 1 has a front portion 4, a rear portion 5, and a crotch portion 6 between the front portion 4 and the rear portion 5. A chassis 11 is provided in the front portion 4, rear portion 5, and crotch portion 6. The chassis 11 may include a topsheet 2 which may be liquid pervious, a backsheet 3 which may be liquid impervious and is associated with the topsheet 2, and an absorbent core (not shown) disposed between the topsheet 2 and the backsheet 3.

In many embodiments, the backsheet 3 may be suitably formed from an appropriate filmic material, for example a laminate including a polymer film and a nonwoven. In some embodiments, the backsheet 3 includes a nonwoven material having a weight in the range of from approximately 7 gsm to approximately 25 gsm (grams per square meter), or in the range of from approximately 10 gsm to approximately 20 gsm, or in the range of from approximately 12 gsm to approximately 18 gsm. In some embodiments, the nonwoven material suitably may include a spunbond material. In some embodiments, the nonwoven material is a polypropylene nonwoven. In some embodiments the polymer film is a polyethylene or polypropylene film. In some embodiments, the nonwoven material suitably may include an entangled or otherwise arranged collection of fibers or filaments that may be thermally bonded or adhesively bonded to a polymer web or backing (e.g., a polyethylene and/or polypropylene backing). Of course, alternately, other known nonwoven materials may be similarly used and/or other known methods for manufacturing the nonwoven material may be employed.

Figure 1B:
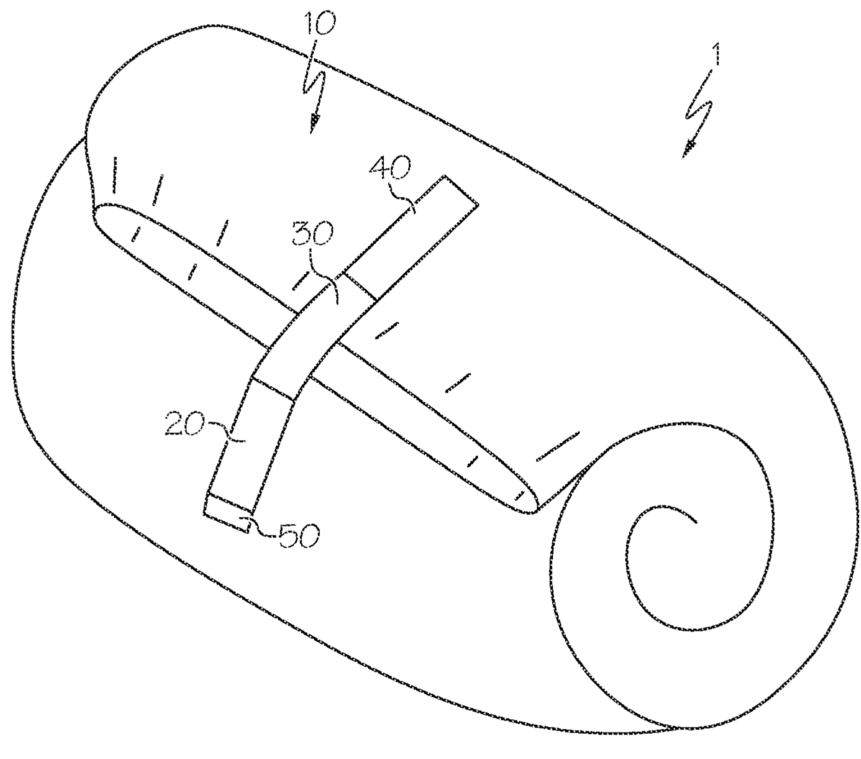
FIG. 1B is a schematic illustration showing a disposable article including a fastening tape assembly, according to aspects described herein.

The disposable article 1 may further include an inner rear panel (not shown) and an outer rear panel 7, each extending from a first side 15 of the disposable article 1 to a second side 16 of the disposable article 1 in the rear portion 5; and an inner front panel 8 and an outer front panel 9 extending from the first side 15 to the second side 16 of the disposable article 1 in the front portion 4. Each of the inner rear panel (not shown) and outer rear panel 7 meet the inner and outer front panels 8 and 9 at each of the first and second sides 15 and 16 of the disposable article 1 at outermost edge lines 17 on each side of the disposable article 1. A portion of the edges 14 of the inner rear panel (not shown) and outer rear panel 7, and inner and outer front panels 8 and 9 define each of two leg openings 12. A portion of the edges 18 of the inner rear panel (not shown) and outer rear panel 7, and inner and outer front panels 8 and 9 define a waist opening 13. The disposable article 1 includes a fastener tape assembly 10 (shown in FIG. 1B) where the fastening component 20 (referred to as 201 in FIGS. 3A-3D) may be viewed on the outer rear panel 7 of the disposable article 1. It will be understood that in some embodiments, the fastening component 20 may be viewed on the outer front panel 9 of the disposable article 1. FIG. 1B also provides an extension component 30 (referred to as 202 in FIGS. 3A-3D) and a bonding component 40 (referred to as 203 in FIGS. 3A-3D). The fastener tape assembly 10 is in an extended position, attached to and securing a rolled up disposable article 1. In some embodiments, the fastener tape assembly 10 may have a fingerlift 50. Although fastener tape assembly 10 is described herein, it will be understood that the subject matter includes other tape assemblies, such as, but not limited to the fastener tape assemblies described in FIGS. 2 and 3A-3D.

Figure 2:
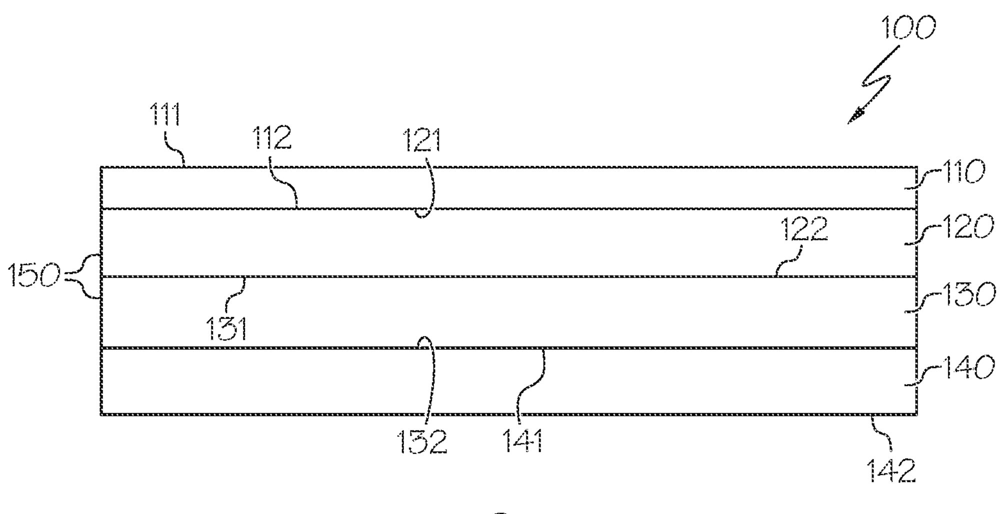
FIG. 2 is an exemplary diagram showing a partial cross sectional view of a fastener tape assembly according to aspects of the disclosure.

FIG. 2 shows an embodiment of a fastener tape assembly 100 (also referred to as 10 in FIG. 1B). The fastener tape assembly includes a carrier component 150 including: (a) a non-woven layer 130 having a first side 131 and a second side 132; (b) a polymer film layer 120 having a first side 121 and a second side 122, (c) an adhesive layer 140 having a first side 141 and a second side 142; (d) a release layer 110 having a first side 111 and a second side 112. The second side 122 of the polymer film layer 120 is at least partially disposed on the first side 131 of the non-woven layer 130. The adhesive layer 140 is at least partially disposed on the second side 132 of the non-woven layer 130. The second side 112 of the release layer 110 is at least partially disposed on the first side 121 of the polymer film layer 120.

Figures 3A, 3B:
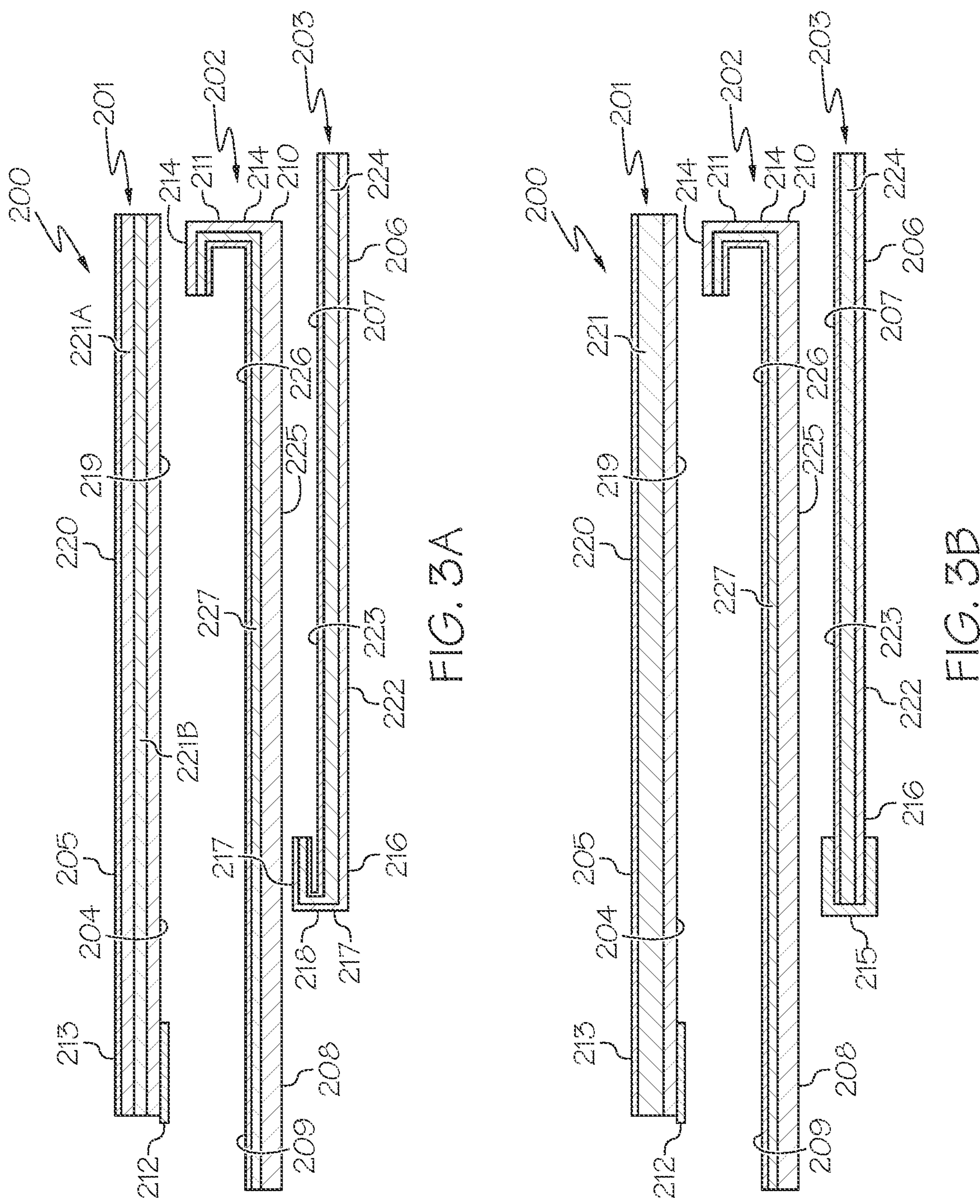
FIG. 3A is a representation of an exploded side view of a z-fold fastener tape assembly according to aspects of the disclosure.
FIG. 3B is a representation of an exploded side view of a z-fold fastener tape assembly according to aspects of the disclosure
Figures 3C, 3D:
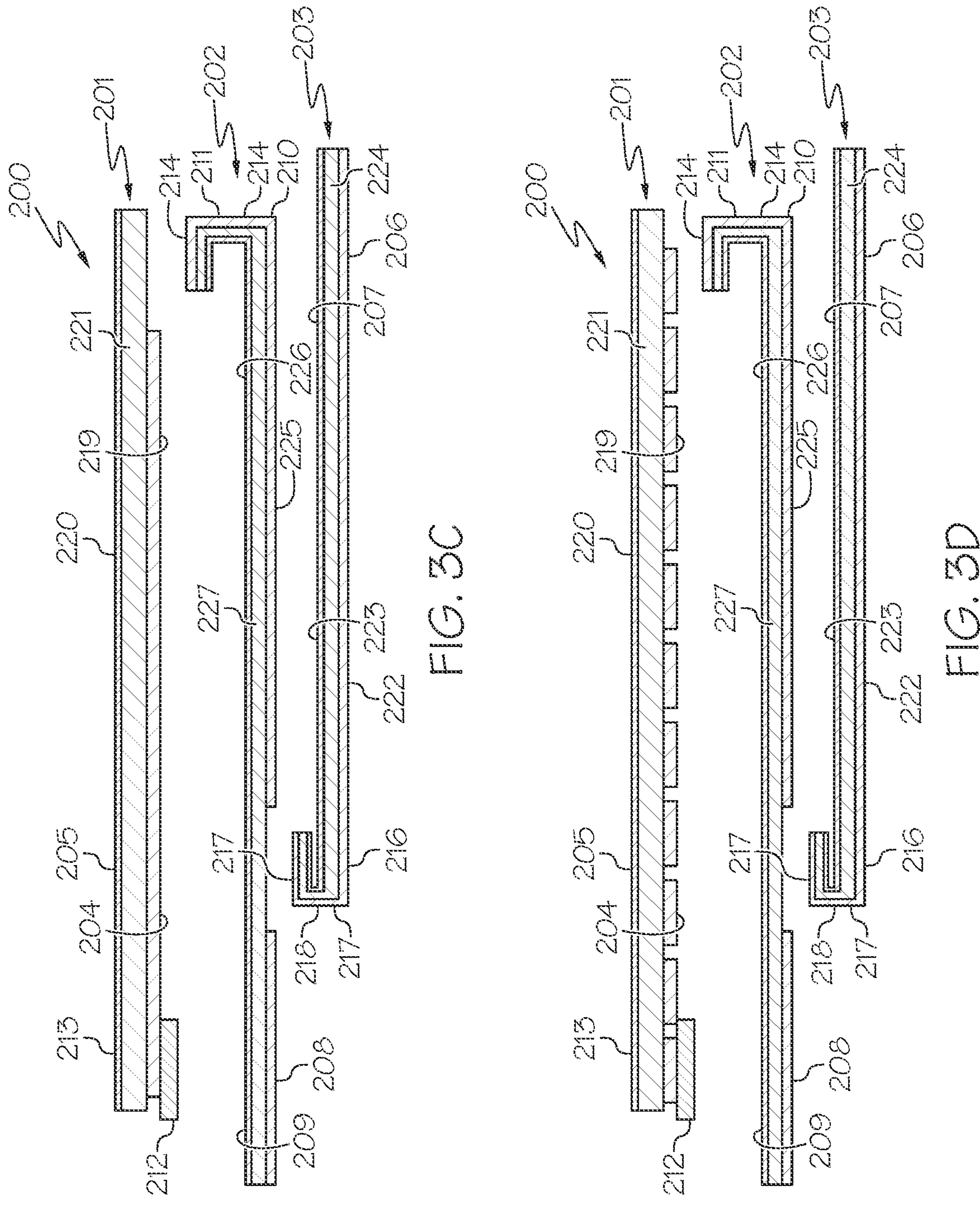
FIG. 3C is a representation of an exploded side view of a z-fold fastener tape assembly according to aspects of the disclosure
FIG. 3D is a representation of an exploded side view of a z-fold fastener tape assembly according to aspects of the disclosure
Figure 3E:
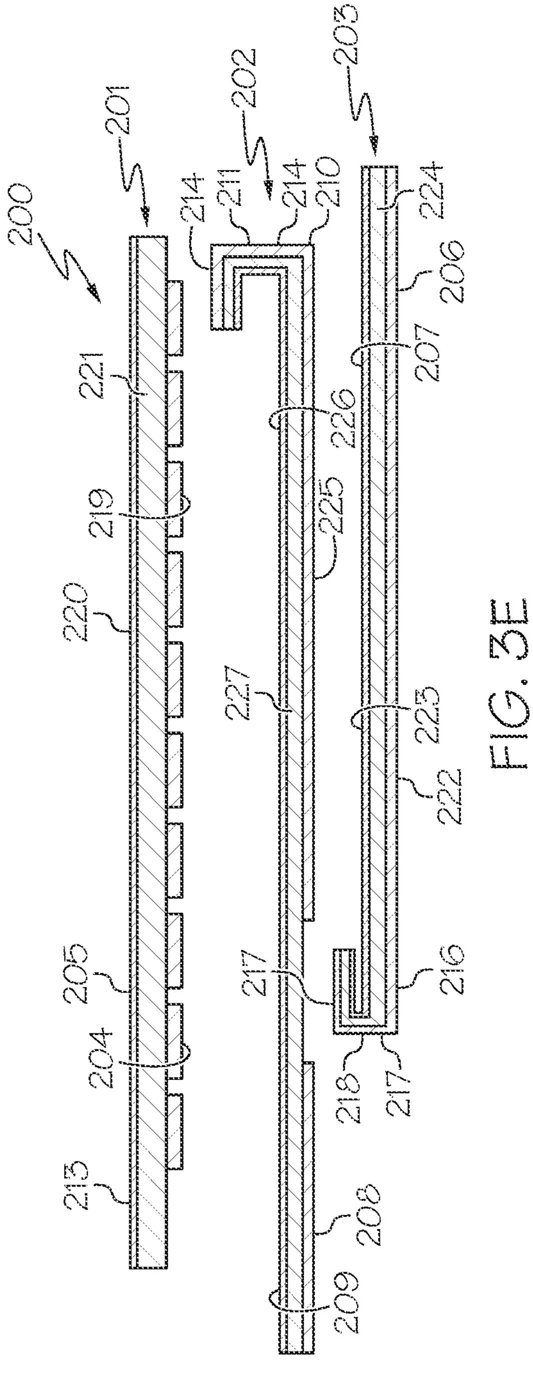
FIG. 3E is a representation of an exploded side view of a z-fold fastener tape assembly according to aspects of the disclosure

FIGS. 3A-3E show embodiments of a z-fold fastener tape assembly 200. The z-fold fastener tape assembly 200 includes: (1) a fastening component 201, (2) a bonding component 203, and (3) a non-extendable extension component 202. The fastening component 201 defines a first face 204 for affixment to a disposable article or substrate and an oppositely directed second face 205. In FIG. 3A, the fastening component 201 includes a carrier component including an adhesive layer 219 at the first face 204 of the fastening component 201; a release layer 220 at the second face 205 of the fastening component 201; a nonwoven layer 221B adjacent to the adhesive layer 219; and a polymer film layer 221A adjacent to the nonwoven layer 221B, such that the nonwoven layer 221B resides between the adhesive layer 219 and the polymer film layer 221A. In FIGS. 3B to 3E, any one of the fastening component, extension component or bonding component can include a carrier component according to aspects of the disclosure, in which case at least one of the carrier layers 221, 227 or 224 includes a polymer film layer and a nonwoven layer (not shown independently; collectively 221 for the fastening component, collectively 227 for the extension component, or collectively 224 for the bonding component) residing adjacent to one another, such that the polymer film layer (not shown independently) is sandwiched between the corresponding nonwoven layer (not shown independently) and the corresponding release layer (220, 226 or 223 respectively), and the nonwoven layer (not shown independently) is sandwiched between the corresponding adhesive layer (219, 225 or 222) and the corresponding polymer film layer (not shown independently). In some embodiments, the fastening component of FIGS. 3B to 3E includes a carrier component according to aspects of the disclosure, including an adhesive layer 219 at the first face 204 of the fastening component; a release layer 220 at the second face 205 of the fastening component 201; a nonwoven layer (as shown in FIG. 3A as 221B) adjacent to the adhesive layer 219; and a polymer film layer (as shown in FIG. 3A as 221A) adjacent to the nonwoven layer (as shown in FIG. 3A as 221B), such that the nonwoven layer (as shown in FIG. 3A as 221B) resides between the adhesive layer 219 and the polymer film layer (as shown in FIG. 3A as 221A). In FIGS. 3A to 3C, the adhesive layer 219 is continuous. In FIGS. 3D and 3E, the adhesive layer 219 is patterned. The bonding component 203 defines a first face 206 for affixment to a disposable article or substrate and an oppositely directed second face 207. At the first face 206 of the bonding component 203 is an adhesive layer 222, and at the second face 207 of the bonding component 203 is a release layer 223. A carrier layer 224 resides between the adhesive layer 222 and the release layer 223. The extension component 202 has a first face 208 and a second face 209, and is generally disposed between the fastening component 201 and the bonding component 203. At the first face 208 of the extension component 202 is an adhesive layer 225, and at the second face 209 of the extension component 202 is a release layer 226. A carrier layer 227 resides between the adhesive layer 225 and the release layer 226. In FIGS. 3A and 3B, the adhesive layer 225 is continuous. In FIGS. 3C to 3E, the adhesive layer 225 is patterned. The fastening component 201 is attached to the extension component 202. A first distal end 210 of the extension component 202 is folded over, forming a folded edge 214 so that the folded edge 214 of the extension component 202 attaches to the first face 204 of the fastening component 201, forming a y-bond 211. Thus, a portion of one end of the extension component 202 is at least partially attached to the fastening component 201. The extension component 202 is attached to the bonding component 203. In FIGS. 3A, 3C to 3E, a first distal end 216 of the bonding component 203 is folded over, forming a folded edge 217 so that the folded edge 217 of the bonding component 203 attaches to the first face 208 of the extension component 203, forming a y-bond 218. In FIG. 3B, a filmic strip 215 is attached to a first distal end 216 of the bonding component 203, forming a U bond that attaches the first distal end 216 of the bonding component 203 with a portion of the first face 208 of the extension component 202. Thus, in each of FIGS. 3A to 3E, a portion of one end of the extension component 202 is at least partially attached to the bonding component 203. In FIGS. 3A-3D, the z-fold fastener tape assembly 200 also has a fingerlift 212 attached to the first face 204 of the fastening component 201, located at a first distal end 213 of the fastening component 201. It will be noted that FIGS. 3A to 3D shows the fastening component 201, extension component 202 and bonding component 203 in exploded view and thus not attached, solely for the purpose of illustrating the different components of the fastener tape assembly 200, however the aforementioned components are attached as described herein.

The following embodiments are contemplated. All combinations of features and embodiments are contemplated.

Embodiment 1: A fastener tape assembly comprising: (1) a carrier component comprising: (a) a non-woven layer having a first side and a second side; and (b) a polymer film layer having a first side and a second side; wherein the second side of the polymer film layer is at least partially disposed on the first side of the non-woven layer; (2) an adhesive layer at least partially disposed on the second side of the non-woven layer; and (3) a release layer at least partially disposed on the first side of the polymer film layer.

Embodiment 2: An embodiment of embodiment 1 wherein the carrier component is extrusion laminated, adhesive bonded, or combinations thereof.

Embodiment 3: An embodiment of any of the embodiments 1-2, wherein the non-woven layer comprises a spunbond non-woven, carded non-woven, spunlace non-woven, meltblown non-woven, or combinations thereof Embodiment 4: An embodiment of any of the embodiments 1-3, wherein the polymer film comprises a polyolefin.

Embodiment 5: An embodiment of any of the embodiments 1-4, wherein the adhesive layer comprises acrylic adhesive, rubber adhesive, silicone adhesive, or combinations thereof.

Embodiment 6: An embodiment of embodiment 5, wherein the rubber adhesive comprises Poly(styrene-butadiene-styrene) (SBS), poly(styrene-isoprene-styrene) (SIS), styrene-butadiene (SB), or combinations thereof.

Embodiment 7: An embodiment of any of the embodiments 1-6, wherein the adhesive layer is pressure sensitive.

Embodiment 8: An embodiment of any of the embodiments 1-7, wherein the adhesive layer is patterned.

Embodiment 9: An embodiment of any of the embodiments 1-7, wherein the adhesive layer is continuous.

Embodiment 10: An embodiment of any of the embodiments 1-9, wherein the release layer comprises a silicone, a fluoropolymer, or combinations thereof.

Embodiment 11: An embodiment of any of the embodiments 1-9, wherein the release layer is a silicone release layer.

Embodiment 12: An embodiment of any of the embodiments 1-11, wherein the release layer is at least partially bonded to the first side of the polymer film layer using heat.

Embodiment 13: An embodiment of any of the embodiments 1-11, wherein the release layer at least partially bonded to the first side of the polymer film layer using UV or IR curing.

Embodiment 14: A z-fold fastener tape assembly comprising: (1) a fastening component defining a first face for affixment to a disposable article or substrate and an oppositely directed second face; (2) a bonding component defining a first face for affixment to a disposable article or substrate and an oppositely directed second face; and (3) an extension component generally disposed between the fastening component and the bonding component and at least partially attached to the fastening component and to the bonding component; wherein at least one of the fastening component, the bonding component, and the extension component comprises the fastener tape assembly of embodiment 1.

Embodiment 15: A z-fold fastener tape assembly comprising: (1) a fastening component defining a first face for affixment to a disposable article or substrate and an oppositely directed second face; (2) a bonding component defining a first face for affixment to a disposable article or substrate and an oppositely directed second face; and (3) an extension component generally disposed between the fastening component and the bonding component and at least partially attached to the fastening component and to the bonding component; wherein the fastening component comprises: (i) a carrier component comprising: (a) a non-woven layer having a first side and a second side; and (b) a polymer film layer having a first side and a second side; wherein the second side of the polymer film layer is at least partially disposed on the first side of the non-woven layer; (ii) an adhesive layer at least partially disposed on the second side of the non-woven layer; and (iii) a release layer at least partially disposed on the first side of the polymer film layer.

Embodiment 16: An embodiment of embodiment 15, wherein the first face of the fastening component is at least partially covered by the adhesive layer to thereby bond the fastening component with the extension component.

Embodiment 17: An embodiment of any of the embodiments 14-15, wherein the adhesive layer on the first face of the fastening component is patterned.

Embodiment 18: An embodiment of any of the embodiments 14-15, wherein the adhesive layer on the first face of the fastening component is continuous.

Embodiment 19: An embodiment of any of the embodiments 14-18, wherein the adhesive layer is pressure sensitive adhesive.

Embodiment 20: An embodiment of any of the embodiments 14-19, wherein the fastening component further comprises hooks.

Embodiment 21: An embodiment of any of the embodiments 14-19, the adhesive layer of the fastening component is provided in an adhesive region on the first face of the fastening component to thereby at least partially bond the fastening component with the extension component.

Embodiment 22: An embodiment of any of the embodiments 14-21 further comprising a finger lift at least partially affixed to the fastening component.

Embodiment 23: An embodiment of any of the embodiments 14-22 further comprising at least one perforation in the bonding component.

Embodiment 24: An embodiment of any of the embodiments 14-23, wherein the fastener tape assembly is in a roll form.

Embodiment 25: A z-fold fastener tape assembly comprising: (1) a fastening component defining a first face for affixment to a disposable article or substrate and an oppositely directed second face; (2) a bonding component defining a first face for affixment to a disposable article or substrate and an oppositely directed second face; and (3) an extension component generally disposed between the fastening component and the bonding component and at least partially attached to the fastening component and to the bonding component; wherein the bonding component comprises: (i) a carrier component comprising: (a) a non-woven layer having a first side and a second side; and (b) a polymer film layer having a first side and a second side; wherein the second side of the polymer film layer is at least partially disposed on the first side of the non-woven layer; (ii) an adhesive layer at least partially disposed on the second side of the non-woven layer; and (iii) a release layer at least partially disposed on the first side of the polymer film layer.

Embodiment 26: An embodiment of embodiment 25, wherein the first face of the bonding component is at least partially covered by the adhesive layer to thereby bond the bonding component with the extension component.

Embodiment 27: An embodiment of any of the embodiments 25-26, wherein the adhesive layer on the first face of the bonding component is patterned.

Embodiment 28: An embodiment of any of the embodiments 25-26, wherein the adhesive layer on the first face of the bonding component is continuous.

Embodiment 29: An embodiment of any of the embodiments 25-28, wherein the adhesive layer is pressure sensitive adhesive.

Embodiment 30: An embodiment of any of the embodiments 25-29, wherein the bonding component further comprises hooks.

Embodiment 31: An embodiment of any of the embodiments 25-30, wherein the adhesive layer of the bonding component is provided in an adhesive region on the first face of the bonding component to thereby at least partially bond the bonding component with the extension component.

Embodiment 32: An embodiment of any of the embodiments 25-31 further comprising at least one perforation in the bonding component.

Embodiment 33: An embodiment of any of the embodiments 25-32, wherein the fastener tape assembly is in a roll form.

Embodiment 34: A z-fold fastener tape assembly comprising: (1) a fastening component defining a first face for affixment to a disposable article or substrate and an oppositely directed second face; (2) a bonding component defining a first face for affixment to a disposable article or substrate and an oppositely directed second face; and (3) an extension component generally disposed between the fastening component and the bonding component and at least partially attached to the fastening component and to the bonding component; wherein the extension component comprises: (i) a carrier component comprising: (a) a non-woven layer having a first side and a second side; and (b) a polymer film layer having a first side and a second side; wherein the second side of the polymer film layer is at least partially disposed on the first side of the non-woven layer; (ii) an adhesive layer at least partially disposed on the second side of the non-woven layer; and (iii) a release layer at least partially disposed on the first side of the polymer film layer.

Embodiment 35: An embodiment of embodiment 34, wherein the first face of the extension component is at least partially covered by the adhesive layer to thereby bond the extension component with the bonding component.

Embodiment 36: An embodiment of embodiment 34, wherein the second face of the extension component is at least partially covered by the adhesive layer to thereby bond the extension component with the fastening component.

Embodiment 37: An embodiment of any of embodiments 34-36, wherein the adhesive layer on the first face of the extension component is patterned.

Embodiment 38: An embodiment of any of embodiments 34-36, wherein the adhesive layer on the first face of the extension component is continuous.

Embodiment 39: An embodiment of any of embodiments 34-38, wherein the adhesive layer is pressure sensitive adhesive.

Embodiment 40: An embodiment of any of embodiments 34-39, wherein the adhesive layer of the extension component is provided in an adhesive region on the first face of the bonding component to thereby at least partially bond the bonding component with the extension component.

Embodiment 41: An embodiment of any of embodiments 34-39, wherein the adhesive layer of the extension component is provided in an adhesive region on the first face of the bonding component to thereby at least partially bond the extension component with the fastening component and the bonding component.

Embodiment 42: An embodiment of any of embodiments 34-41 further comprising at least one perforation in the bonding component.

Embodiment 43: An embodiment of any of embodiments 34-44, wherein the fastener tape assembly is in a roll form.

Embodiment 44: A z-fold fastener tape assembly comprising: a fastening component defining a first face for affixment to a disposable article or substrate and an oppositely directed second face; a bonding component defining a first face for affixment to a disposable article or substrate and an oppositely directed second face; and an extension component generally disposed between the fastening component and the bonding component and at least partially attached to the fastening component and to the bonding component; wherein the extension component comprises a first face and a second face; wherein the extension component is substantially non-extendable; and wherein at least one of the fastening component and the bonding component comprises the fastener tape assembly of Claim 1.

Embodiment 45: An embodiment of embodiment 44, wherein the extension component comprises a polyester.

Embodiment 46: An embodiment of embodiment 44, wherein the extension component comprises polyethylene terephthalate (PET), oriented polypropylene (OPP), BOPP, or any combination thereof.

Embodiment 47: An embodiment of any of embodiments 44-47, wherein the first face of the extension component is at least partially covered by an adhesive layer.

Embodiment 48: An embodiment of any of embodiments 44-47, wherein the second face of the extension component is at least partially covered by a release layer.

Embodiment 49: A method of making the z-fold fastener tape assembly of any of embodiments 14-48.

Embodiment 50: An article including the z-fold fastener tape assembly of any of embodiments 14-48.

Embodiment 51: An embodiment of embodiment 50, wherein the article is a diaper.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art (for example, features associated with certain configurations of the invention may instead be associated with any other configurations of the invention, as desired).

Therefore, the above-described embodiments should be regarded as illustrative rather than restrictive. Accordingly, it should be appreciated that variations to those embodiments can be made by those skilled in the art without departing from the scope of the invention as defined by the following claims.

EXAMPLES

Ageing Tests

The unwind release force of a fastener tape assembly according to aspects of this disclosure was compared to the unwind release force of three different conventional tapes. The conventional tapes had a siliconized nonwoven laminated with a polyolefin layer. A summary of the tape assemblies and comparative tapes tested can be found in Table 1 below. As can be seen from Table 1, the same adhesive was used in Examples 1-3 (PSA); while different adhesives PSA-C1, PSA-C2 and PSA-C3 were used in Comparative Example 1; Comparative Examples 2 and 3; and Comparative Examples 4 and 5, respectively. Each of the adhesives used in the Examples and Comparative Examples were pressure sensitive rubber-based adhesives. The silicone coating weight on each of the comparative tapes was varied, as shown in Table 1 below. Unwind release testing, which was conducted on rolls of tape each having a width of 66 mm, was performed, using an Instron® Model 5943 tensile tester (manufactured by Instron Corporation, Massachusetts, USA), at an unwind speed of 1000 mm/min. Testing was repeated on each tape at one week intervals, over a period of six weeks. In between testing, the tapes were stored at a temperature of 50° C.

TABLE 1

| Tape Constructions | | | |
|---|---|---|---|
| Example | Comparative Example | Adhesive | Silicone Weight |
| 1 | | PSA | low |
| | 1 | PSA-C1 | high |
| 2 | | PSA | Low |
| | 2 | PSA-C2 | medium |
| | 3 | PSA-C2 | high |
| 3 | | PSA | low |
| | 4 | PSA-C3 | medium |
| | 5 | PSA-C3 | high |

Figure 4:
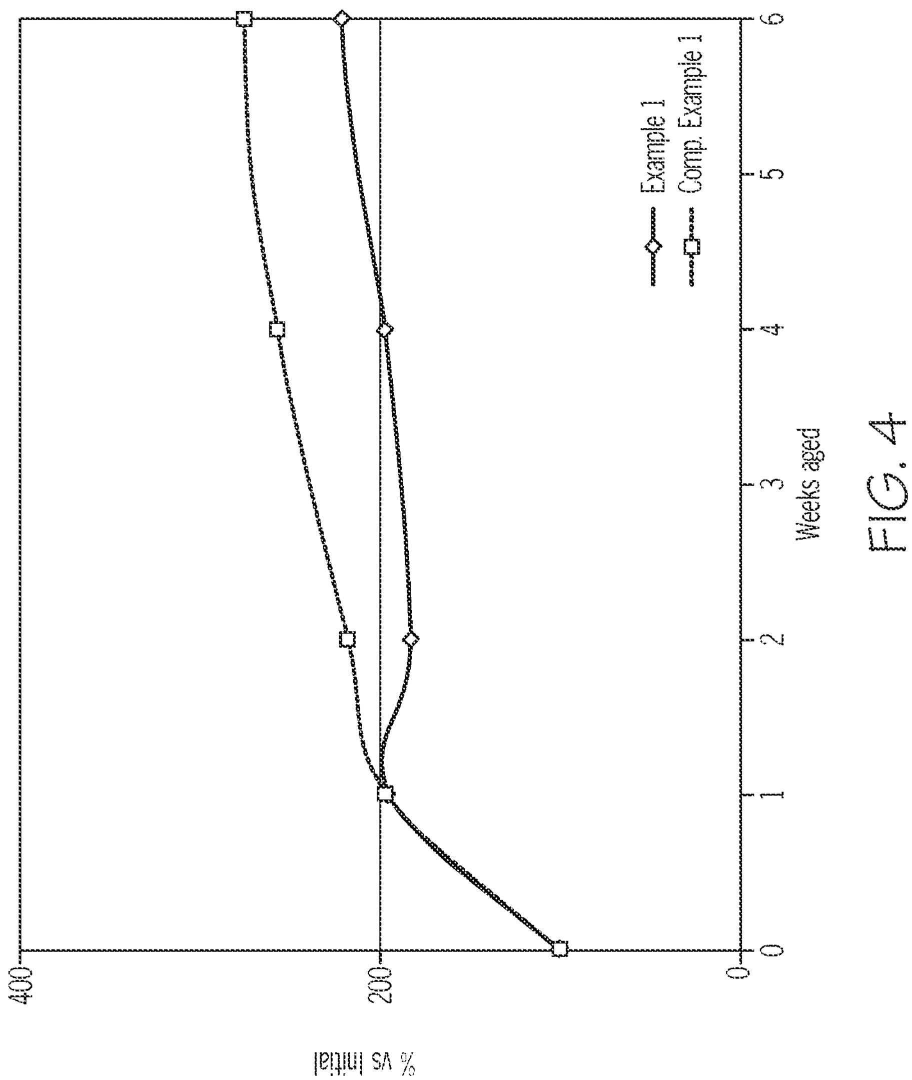
FIG. 4 is a chart showing the % unwind release force, versus the initial unwind release force, of a fastener tape assembly according to an embodiment of the disclosure, and of a conventional tape, over a period of 6 weeks.
Figure 5:
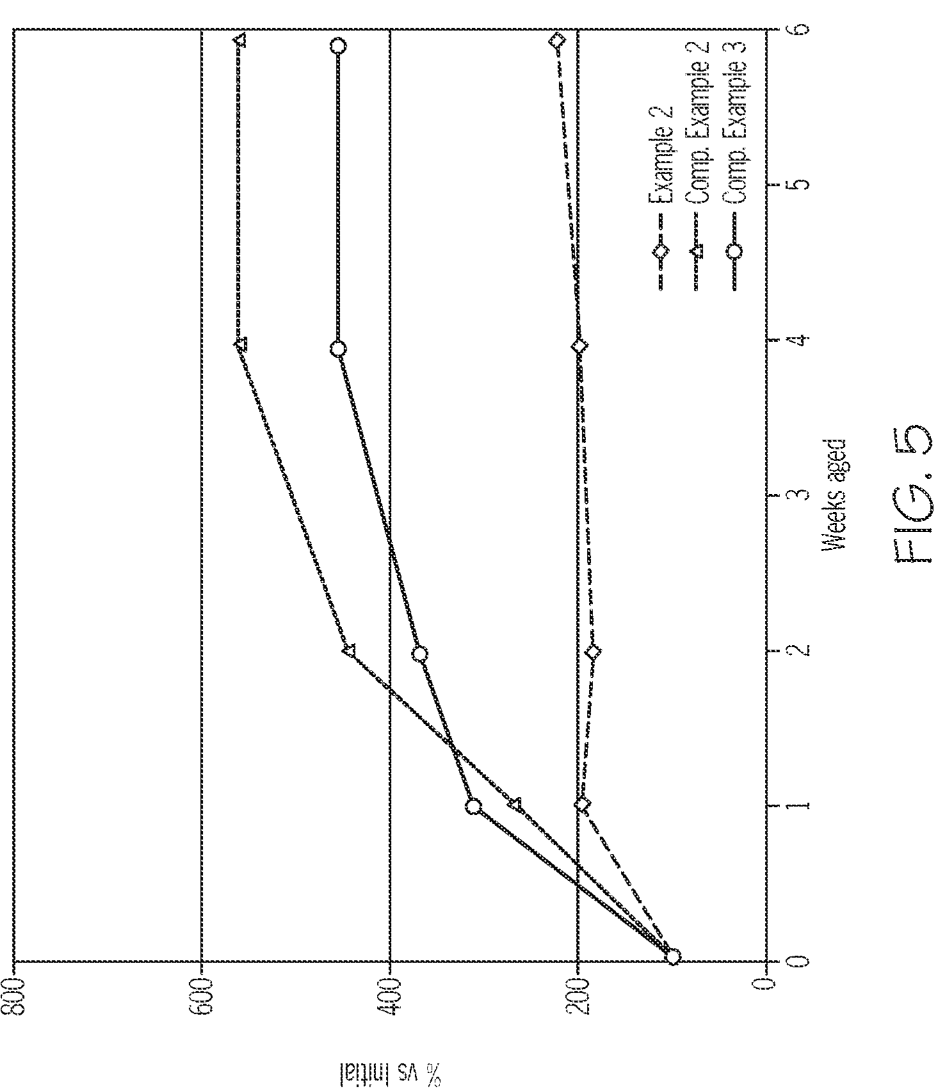
FIG. 5 is a chart showing the percent unwind release force, versus the initial unwind release force, of a fastener tape assembly according to an embodiment of the disclosure, and of two conventional tapes, over a period of 6 weeks.
Figure 6:
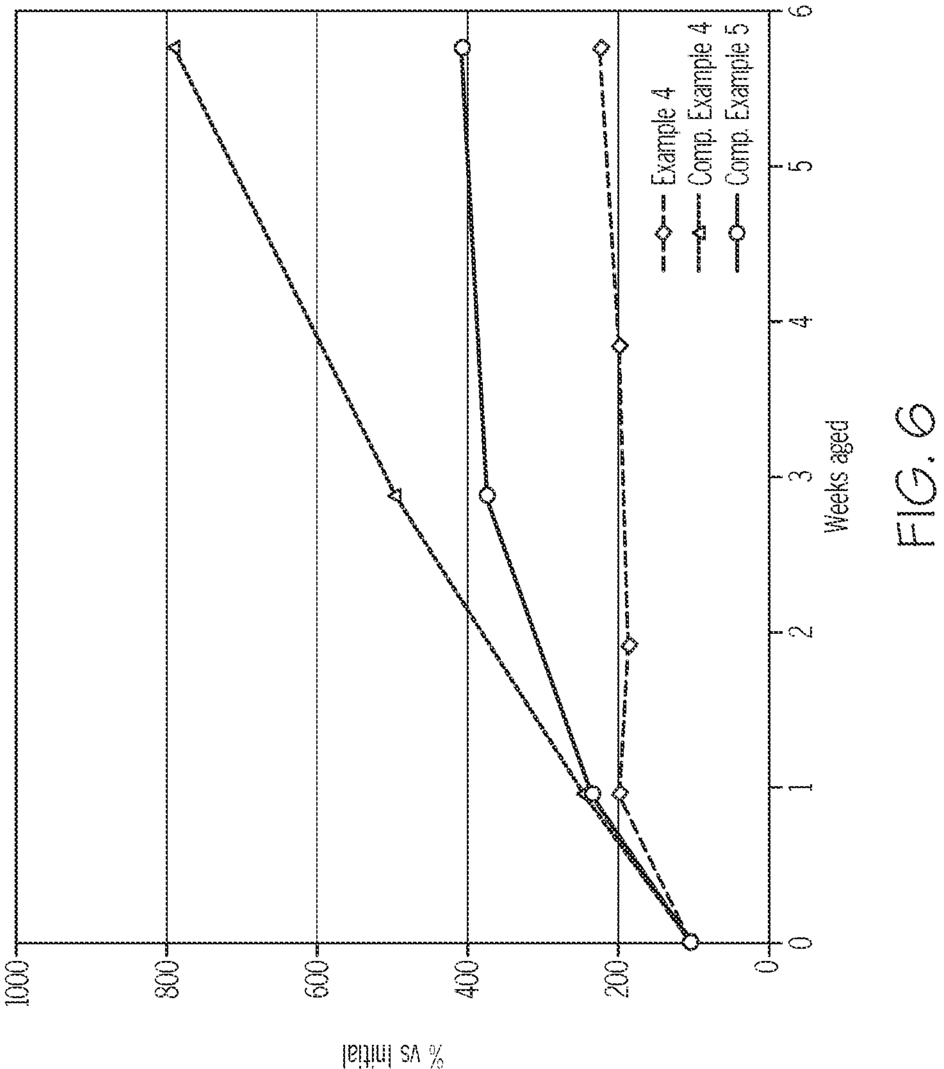
FIG. 6 is a chart showing the percent unwind release force, versus the initial unwind release force, of a fastener tape assembly according to an embodiment of the disclosure, and of two conventional tapes, over a period of 6 weeks.

The results of the ageing testing can be found in Table 2 below, and in FIGS. 4 to 6.

TABLE 2

| Unwind Release Results | | |
|---|---|---|
| Example | Comparative Example | Results |
| 1 | | Clean unwind |
| | 1 | Nonwoven damage as of 6 weeks |
| 2 | | Clean unwind |
| | 2 | Nonwoven damage as of 3 weeks |
| | 3 | Clean unwind |
| 3 | | Clean unwind |
| | 4 | Nonwoven damage as of 3 weeks |
| | 5 | Clean unwind |

As can be seen from the ageing results, the tape assembly according to the disclosure unwound cleanly, even after 6 weeks, and even with a low silicone coating weight. In contrast, the conventional tapes experienced an at least partial transfer of adhesive onto the nonwoven of the neighboring tape layer, which undesirably resulted in nonwoven fibers being pulled out from the nonwoven layer upon unwinding of the tape, thereby causing damage to the nonwoven. As a result, as shown in Table 2, the conventional tapes experienced nonwoven damage for tapes having a medium silicone coat weight, and required a high silicone coating weight in order to achieve a clean unwind. FIGS. 5-6 show how the tape release force behaved at different time intervals, as compared to the initial unwind release force, for each example.

Elongation Tests

Figure 7:
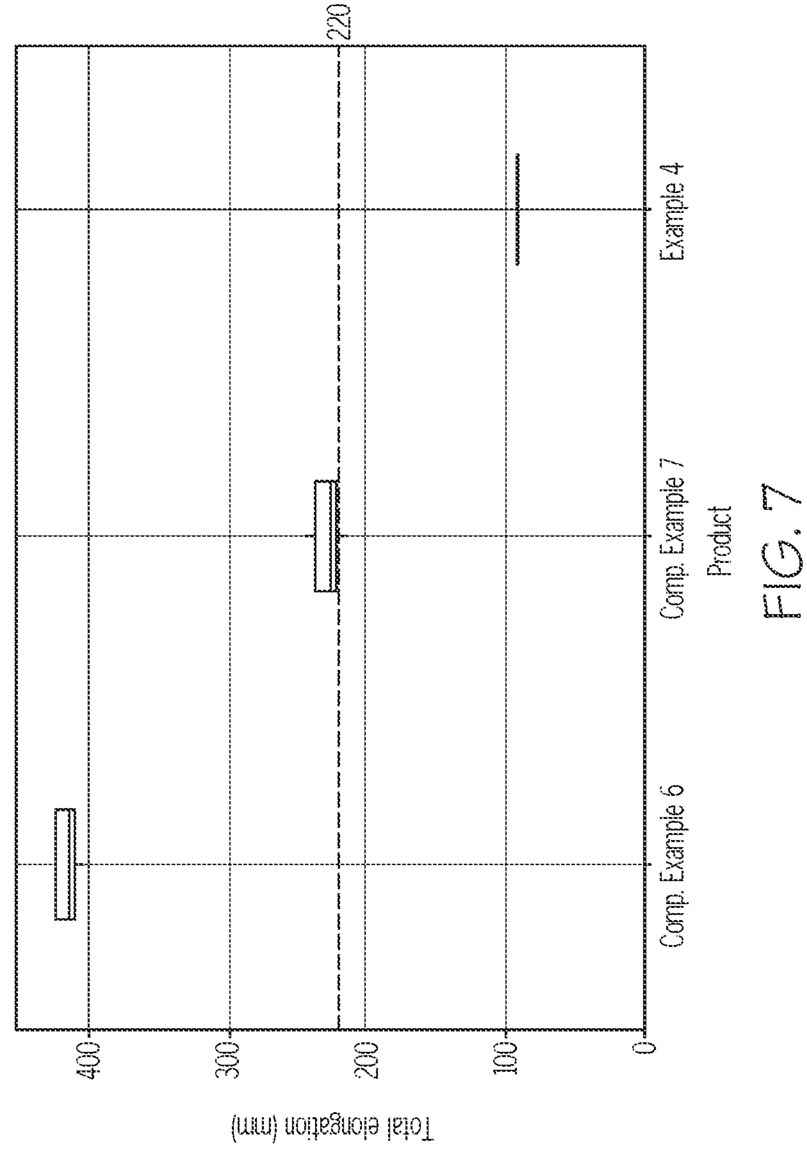
FIG. 7 is a chart showing the total elongation of (i) a z-fold fastener tape assembly having a nonextendable extension component, according to an embodiment of the disclosure, and (ii) two conventional z-fold tapes.

The total elongation of a z-fold fastener tape assembly according to an embodiment of this disclosure (Example 4) was compared to the total elongation of two conventional z-fold tapes (Comparative Examples 6 and 7). The material of construction of each of the z-fold tapes is shown in Table 3, below. The nonwoven laminate of Example 4's fastening component was a fastening tape assembly including a rubber based pressure sensitive adhesive layer adjacent to a nonwoven layer, which nonwoven was adjacent to a polyolefin polymer film, which polymer film was adjacent to a silicone release layer. Elongation testing was performed on tapes having a width of 13 mm, using an Instron® Model 5943 tensile tester (manufactured by Instron Corporation, Massachusetts, USA), at an elongation speed of 1500 mm/min. The increase in each tape's gauge length at a rupture or break was recorded. The total elongation of each tape was calculated by adding the increase in tape length after elongation to the original tape length. The results of the total elongation testing are shown in FIG. 7. The total elongation of Example 4, which included the fastening tape assembly of the disclosure as the fastening component, and a non-elongatable polyester extension component, had a total elongation that was significantly less than that of Comparative Examples 6 and 7. As can be seen from FIG. 7, the total elongation of Comparative Example 6 was approximately four times that of Example 4, while the total elongation of Comparative Example 6 over twice that of Example 4.

TABLE 3

| Z-Fold Construction | | | |
|---|---|---|---|
| Example | Fastening Component | Extension Component | Bonding Component |
| Comparative Ex. 6 | cast polypropylene | cast polypropylene | BOPP |
| Comparative Ex. 7 | cast polypropylene | polyester | BOPP |
| Example 4 | nonwoven laminate | polyester | BOPP |

What is claimed is:

1. A z-fold fastener tape assembly comprising:

a fastening component defining a first face for affixment to a disposable article or substrate and an oppositely directed second face;

a bonding component defining a first face for affixment to a disposable article or substrate and an oppositely directed second face; and an extension component disposed between the fastening component and the bonding component and at least partially attached to the first face of the fastening component and to the first face of the bonding component;

wherein at least one of the fastening component, the bonding component, and the extension component comprises a fastener tape assembly, wherein the fastener tape assembly comprises:

a carrier component comprising:

a non-woven layer having a first side and a second side; and a polymer film layer having a first side and a second side;

wherein the second side of the polymer film layer is at least partially disposed on the first side of the non-woven layer;

an adhesive layer at least partially disposed on the second side of the non-woven layer; and a distinct release layer separate from the polymer film layer, at least partially disposed on the first side of the polymer film layer, wherein the fastener tape assembly has a release coat weight of less than 6 $g/m^2$.

2. The z-fold fastener tape assembly of claim 1, wherein the first face of the fastening component is at least partially covered by the adhesive layer to thereby bond the fastening component with the extension component.

3. The z-fold fastener tape assembly of claim 1, wherein the adhesive layer is pressure sensitive adhesive.

4. The z-fold fastener tape assembly of claim 1, wherein the fastening component further comprises hooks.

5. The z-fold fastener tape assembly of claim 1, wherein the adhesive layer of the fastening component is provided in an adhesive region on the first face of the fastening component to thereby at least partially bond the fastening component with the extension component.

6. The z-fold fastener tape assembly of claim 1 further comprising a finger lift at least partially affixed to the fastening component.

7. The z-fold fastener tape assembly of claim 1 further comprising at least one perforation in the bonding component.

8. A method of making the z-fold fastener tape assembly of claim 1.

9. An article including the z-fold fastener tape assembly of claim 1.

10. The article of claim 9, wherein the article is a diaper.

11. A z-fold fastener tape assembly comprising:

a fastening component defining a first face for affixment to a disposable article or substrate and an oppositely directed second face;

a bonding component defining a first face for affixment to a disposable article or substrate and an oppositely directed second face; and an extension component generally disposed between the fastening component and the bonding component and at least partially attached to the fastening component and to the bonding component;

wherein the fastening component comprises:

a carrier component comprising: (a) a non-woven layer having a first side and a second side; and (b) a polymer film layer having a first side and a second side; wherein the second side of the polymer film layer is at least partially disposed on the first side of the non-woven layer;

an adhesive layer at least partially disposed on the second side of the non-woven layer; and a distinct release layer separate from the polymer film layer, at least partially disposed on the first side of the polymer film layer.

12. A z-fold fastener tape assembly comprising:

a fastening component defining a first face for affixment to a disposable article or substrate and an oppositely directed second face;

a bonding component defining a first face for affixment to a disposable article or substrate and an oppositely directed second face; and an extension component generally disposed between the fastening component and the bonding component and at least partially attached to the fastening component and to the bonding component;

wherein the bonding component comprises:

a carrier component comprising: (a) a non-woven layer having a first side and a second side; and (b) a polymer film layer having a first side and a second side; wherein the second side of the polymer film layer is at least partially disposed on the first side of the non-woven layer;

an adhesive layer at least partially disposed on the second side of the non-woven layer; and a distinct release layer separate from the polymer film layer, at least partially disposed on the first side of the polymer film layer.

13. The z-fold fastener tape assembly of claim 12, wherein the first face of the bonding component is at least partially covered by the adhesive layer to thereby bond the bonding component with the extension component.

14. The z-fold fastener tape assembly of claim 12, wherein the adhesive layer is pressure sensitive adhesive.

15. The z-fold fastener tape assembly of claim 12, wherein the bonding component further comprises hooks.

16. The z-fold fastener tape assembly of claim 12, wherein the adhesive layer of the bonding component is provided in an adhesive region on the first face of the bonding component to thereby at least partially bond the bonding component with the extension component.

17. The z-fold fastener tape assembly of claim 12 further comprising at least one perforation in the bonding component.

18. A z-fold fastener tape assembly comprising:

a fastening component defining a first face for affixment to a disposable article or substrate and an oppositely directed second face;

a bonding component defining a first face for affixment to a disposable article or substrate and an oppositely directed second face; and an extension component generally disposed between the fastening component and the bonding component and at least partially attached to the fastening component and to the bonding component;

wherein the extension component comprises:

a carrier component comprising: (a) a non-woven layer having a first side and a second side; and (b) a polymer film layer having a first side and a second side; wherein the second side of the polymer film layer is at least partially disposed on the first side of the non-woven layer;

an adhesive layer at least partially disposed on the second side of the non-woven layer; and a distinct release layer separate from the polymer film layer, at least partially disposed on the first side of the polymer film layer.

19. The z-fold fastener tape assembly of claim 18, wherein the first face of the extension component is at least partially covered by the adhesive layer to thereby bond the extension component with the bonding component.

20. The z-fold fastener tape assembly of claim 18, wherein the second face of the extension component is at least partially covered by the adhesive layer to thereby bond the extension component with the fastening component.

21. The z-fold fastener tape assembly of claim 18, wherein the adhesive layer is pressure sensitive adhesive.

22. The z-fold fastener tape assembly of claim 18, wherein the adhesive layer of the extension component is provided in an adhesive region on the first face of the extension component to thereby at least partially bond the bonding component with the extension component.

23. The z-fold fastener tape assembly of claim 18 wherein the adhesive layer of the extension component is provided in an adhesive region on the first face of the extension component to thereby at least partially bond the extension component with the fastening component and the bonding component.

24. The z-fold fastener tape assembly of claim 18 further comprising at least one perforation in the bonding component.

25. A z-fold fastener tape assembly comprising:

a fastening component defining a first face for affixment to a disposable article or substrate and an oppositely directed second face;

a bonding component defining a first face for affixment to a disposable article or substrate and an oppositely directed second face; and an extension component disposed between the fastening component and the bonding component and at least partially attached to the first face of the fastening component and to the first face of the bonding component;

wherein the extension component comprises a first face and a second face;

wherein the extension component is substantially non-extendable; and wherein at least one of the fastening component and the bonding component comprises a fastener tape assembly, wherein the fastener tape assembly comprises:

a carrier component comprising:

a non-woven layer having a first side and a second side; and a polymer film layer having a first side and a second side;

wherein the second side of the polymer film layer is at least partially disposed on the first side of the non-woven layer;

an adhesive layer at least partially disposed on the second side of the non-woven layer; and a distinct release layer separate from the polymer film layer, at least partially disposed on the first side of the polymer film layer, wherein the fastener tape assembly has a release coat weight of less than 6 g/$m^2$.

26. The z-fold fastener tape assembly of claim 25, wherein the extension component comprises a polyester.

27. The z-fold fastener tape assembly of claim 25, wherein the extension component comprises polyethylene terephthalate (PET), oriented polypropylene (OPP), BOPP, or any combination thereof.

28. The z-fold fastener tape assembly of claim 25, wherein the first face of the extension component is at least partially covered by an adhesive layer.

29. The z-fold fastener tape assembly of claim 25, wherein the second face of the extension component is at least partially covered by a release layer.

* * * * *